United States Patent
Pelus et al.

(10) Patent No.: US 11,459,545 B2
(45) Date of Patent: Oct. 4, 2022

(54) METHODS TO ENHANCE DELIVERY AND ENGRAFTMENT OF STEM CELLS INCLUDING THE IDENTIFICATION OF SPECIFIC PROSTAGLANDIN E2 RECEPTORS

(75) Inventors: Louis M. Pelus, Indianapolis, IN (US); Jonathan Hoggatt, Cambridge, MA (US)

(73) Assignee: INDIANA UNIVERSITY RESEARCH AND TECHNOLOGY CORPORATION, Bloomington, IN (US)

( * ) Notice: Subject to any disclaimer, the term of this patent is extended or adjusted under 35 U.S.C. 154(b) by 0 days.

(21) Appl. No.: 13/509,409

(22) PCT Filed: Nov. 15, 2010

(86) PCT No.: PCT/US2010/056744
§ 371 (c)(1),
(2), (4) Date: Aug. 20, 2012

(87) PCT Pub. No.: WO2011/060381
PCT Pub. Date: May 19, 2011

(65) Prior Publication Data
US 2012/0315253 A1 Dec. 13, 2012

Related U.S. Application Data

(60) Provisional application No. 61/261,349, filed on Nov. 15, 2009, provisional application No. 61/261,352, filed on Nov. 15, 2009.

(51) Int. Cl.
*C12N 5/0789* (2010.01)

(52) U.S. Cl.
CPC ........ *C12N 5/0647* (2013.01); *C12N 2501/02* (2013.01)

(58) Field of Classification Search
CPC ... C12N 5/0647; C12N 2501/02; A61P 43/00; A61P 7/00
See application file for complete search history.

(56) References Cited

U.S. PATENT DOCUMENTS

2005/0266555 A1 12/2005 Lu et al.

FOREIGN PATENT DOCUMENTS

| CA | 2666972 A1 * | 6/2008 |
| WO | WO 2006/101867 A2 | 9/2006 |

(Continued)

OTHER PUBLICATIONS

Arikawa et al., Regulation of Bone Morphogenetic Protein-2 Expression by Endogenous Prostaglandin E2 in Human Mesenchymal Stem Cells, 2004, Journal of Cellular Physiology 200(3): 400-406.*

(Continued)

*Primary Examiner* — Sean C. Barron
(74) *Attorney, Agent, or Firm* — Quarles & Brady LLP

(57) ABSTRACT

The receptor $EP_4$ is identified as the $PGE_2$ receptor that is most responsible enhancing the homing and engraftment of hematopoietic stem and progenitor cells. Treatment of graft sources and graft recipients with compounds that preferentially target the $EP_4$ receptor provide effective methods of increasing engraftment success while minimizing adverse side effects that may be associated with therapies that include the use of less selective molecules such as $PGE_2$ and $dmPGE_2$. One effective molecule used in such therapies is 5-[(1E,3R)-4,4-difluoro-3-hydroxy-4-phenyl-1-buten-1-yl]-1-[6-(2H-tetrazol-5R-yl)hexyl]-2-pyrrolidinone or a pharmaceutically acceptable salt thereof (L-902, 688).

10 Claims, 2 Drawing Sheets

(56) References Cited

FOREIGN PATENT DOCUMENTS

| WO | WO 2007/112084 A2 | 10/2007 |
| WO | WO200712084 A1 | 10/2007 |
| WO | WO 2008/070310 A2 | 6/2008 |
| WO | WO 2008/073748 A1 | 6/2008 |
| WO | WO 2010/108028 A2 | 9/2010 |

OTHER PUBLICATIONS

Foudi et al., Vasorelaxation induced by prostaglandin E2 in human pulmonary vein: role of the EP4 receptor subtype, 2008, British Journal of Pharmacology 154: 1631-1639.*

Steidl et at, Primary human CD34_ hematopoietic stem and progenitor cells express functionally active receptors of neuromediators, 2004, Blood 104(1) : 81-88.*

North et al., Prostaglandin E2 regulates vertebrate haematopoietic stem cell homeostasis, 2007, Nature, 447: 1007-1011.*

Kunikata et al., 16,16-Dimethyl Prostaglandin E2 Inhibits Indomethacin-Induced Small Intestinal Lesions Through EP3 and EP4 Receptors, Digestive Diseases and Sciences, 47(4): 894-904.*

Lord et al., Prostaglandin E2 Making More of Your Marrow, 2007, Cell Cycle 6:24, 3054-3057.*

Broxmeyer, Mechanism Unknown: Prostaglandin E2May Improve HSC Therapies, 2007, Cell Stem Cell, 1(2): 135-136 (Year: 2007).*

Challen et al, Mouse Hematopoietic Stem Cell Identification and Analysis, 2009, Cytometry A. 75(1): 14-24 (Year: 2009).*

Yoshida et al. Stimulation of bone formation and prevention of bone loss by prostaglandin E EP4 receptor activation. PNAS (2002), 99(7), 4580-4585. (Year: 2002).*

Domen et al. Bone Marrow (Hematopoietic) Stem Cells. Chapter 2 in Regenerative Medicine (2006), Department of Health and Human Services, p. 13-34. (Year: 2006).*

Suzawa et al. The Role of Prostaglandin E Receptor Subtypes (EP1, EP2, EP3, and EP4) in Bone Resorption: An Analysis Using Specific Agonists for the Respective EPs. Endocrinology (2000), 141, 1554-1559. (Year: 2000).*

Milne et al. Comparison of the EP Receptor Subtypes Mediating Relaxation of the Rabbit Jugular and Pig Saphenous Veins. Prostaglandins (1995), 49, 225-237. (Year: 1995).*

Hoggatt et al. Prostaglandin E2 Enhances Survival, Proliferation, Homing and Engraftment of Mouse Hematopoietic Stem Cells. Blood (epub. Nov. 16, 2008), 112(11), 74. (Year: 2008).*

International Searching Authority, International Search Report for PCT/US10/56744, dated Jan. 2011.

International Searching Authority, Written Opinion for PCT/US10/56744, dated Jan. 2011.

International Searching Authority, International Preliminary Report on Patentability for PCT/US10/56744, dated May 2012.

Foudi, et al., Vasorelaxation Induced by Prostaglandin E2 in Human Pulmonary Vein: Role of the EP4 Receptor Subtype. British Journal of Pharmacology, 2008, vol. 154, pp. 1631-1639.

Bayer, M., Supplementary European Search Report for EP App. No. 10830872.7, dated Apr. 16, 2013, pp. 1-2, Munich.

European Search Opinion for EP App. No. 10830872.7, dated Apr. 25, 2013, pp. 1-3.

Hoggatt, J., et al., Prostaglandin E2 enhances hematopoietic stem cell homing, survival, and proliferation, Blood, Mar. 26, 2009, pp. 5444-5455, vol. 113, No. 22.

Pittenger, M.F., et al., Multilineage Potential of Adult Human Mesenchymal Stem Cells, Science, Apr. 2, 1999, pp. 143-147, vol. 284.

Machwate et al., "Prostaglandin receptor $EP_4$ mediates the bone anabolic effects of $PGE_2$," Mol. Pharmacol., 60:36-41 (2001).

Luu et al., "Pharmacokinetic-pharmacodynamic and response sensitization modeling of the intraocular pressure-lowering effect of the EP4 agonist 5-{3-[(2S)-2-{(3R)-3-hydroxy-4-[3-(trifuluoromethyl)phenyl]butyl}-5-oxoprrolidin-1-yl]propyl}thiophene-2-carboxylate (PF-04475270)," J. Pharmacol. Exp. Ther., 331:627-635 (2009).

Maruyama et al., "Design and synthesis of a selective EP4-receptor agonist. Part 4: practical synthesis and biological evaluation of a novel highly selective EP4-receptor agonist," Bioorg. Med. Chem., 10:2103-2110 (2002).

* cited by examiner

METHODS TO ENHANCE DELIVERY AND ENGRAFTMENT OF STEM CELLS INCLUDING THE IDENTIFICATION OF SPECIFIC PROSTAGLANDIN E2 RECEPTORS

PRIORITY CLAIM

Cross-Reference to Related Applications

This application is a nationalization of PCT Patent Application Serial No. PCT/US2010/056744 Nov. 15, 2010, which claims the benefit of U.S. Provisional Application Nos. 61/261,352 filed Nov. 15, 2009 and 61/261,349 filed Nov. 15, 2010, the disclosures of which are expressly incorporated herein by reference.

STATEMENT OF GOVERNMENTAL RIGHTS

This invention was made with government support under grant number HL069669 awarded by the National Institutes of Health. The government has certain rights in the invention.

FIELD OF THE INVENTION

Methods of treating potential cell grafts comprising hematopoietic stem and progenitor cells with a selective receptor agonist of the $EP_4$ receptor to enhance their homing, survival, self-renewal and proliferation.

BACKGROUND

Bone marrow transplantation, including the more popular procedures of mobilized peripheral blood stem cell transplantation and umbilical cord blood transplantation are routinely used as curative procedures for malignant and nonmalignant hematologic diseases and genetic disorders. These procedures require that hematopoietic grafts containing sufficient numbers of stems and progenitor cell populations be harvested from healthy normal donors or from patients at a time of low or absent disease and subsequently administered to patients whose hematopoietic system and presumably disease tissue has been eradicated. After transplantation, the appropriate stem cells travel to or "home" to the appropriate bone marrow micro-environmental niches. Once lodged within the appropriate niches, these cells proliferate and produce new stem cells, a process called self-renewal. The cells also differentiate into lineage restricted progenitor cells and mature cells, thereby restoring the blood forming hematopoietic system for the life of the recipient. Progenitor cells are required in said grafts to also produce mature cells; however since they are not stem cells and cannot self-renew, their participation is limited in lifespan. Successful transplantation procedures require that sufficient cells be collected from the donor and administered to the recipient. The need for large numbers of cells is aggravated by the fact that collection procedures and the process of homing and engraftment are stressful to the graft cells resulting in the loss of a portion of the cells in the graft.

In particular, umbilical cord blood grafts contain limited numbers of stem cells and for this reason usually cannot be routinely used to transplant adults. Similarly, 10-25% of normal donors and up to 75% of specific patient populations, particularly those exposed to certain chemotherapeutic agents, e.g., fludarabine, fail to mobilize sufficient cells for use in transplant procedures. In general, the greater the number of viable cells that can be transplanted the greater the chances are for a successful treatment. Accordingly, there is a need for novel agents and/or methodologies that can increase the number of hematopoietic stem cells or progenitor cells in the transplant or alternatively to facilitate or enhance their homing to bone marrow. Some aspects of the current invention seek to address this need.

SUMMARY

Some aspects of the present invention provided methods of treating a donor or donor cells or a recipient of hematopoietic stem or progenitor cells, comprising the steps of providing at least one compound that preferentially interacts with the $PGE_2$ $EP_4$ receptor, on hematopoietic stem or progenitor cells, or a pharmaceutically acceptable salt thereof and administering a therapeutically acceptable dose of said compound to a patient in need thereof. These compounds may be selected from the group consisting of: 2-[3-[(1R,2S,3R)-3-hydroxy-2-[(E,3S)-3-hydroxy-5-[2-(methoxymethyl)phenyl]pent-1-enyl]-5-oxocyclopentyl]sulfanylpropylsulfanyl]acetic acid; methyl 4-[2-[(1R,2R,3R)-3-hydroxy-2-[(E,3S)-3-hydroxy-4-[3-(methoxymethyl)phenyl]but-1-enyl]-5-oxocyclopentyl]ethylsulfanyl]butanoate; 16-(3-Methoxymethyl)phenyl-ω-tetranor-5-thiaPGE; 5-{3-[(2S)-2-{(3R)-3-hydroxy-4-[3-(trifluoromethyl)phenyl]butyl}-5-oxopyrrolidin-1-yl]propyl]thiophene-2-carboxylate; [4'-[3-butyl-5-oxo-1-(2-trifluoromethyl-phenyl)-1,5-dihydro-[1,2,4]triazol-4-ylmethyl]-biphenyl-2-sulfonic acid (3-methyl-thiophene-2-carbonyl)-amide]; and ((Z)-7-{(1R,4S,5R)-5-[(E)-5-(3-chloro-benzo [b]thiophene-2-yl)-3-hydroxy-pent-1-enyl]-4-hydroxy-3,3-dimethyl-2-oxo-cyclopentyl}-hept-5-enoic acid)

In some embodiments the compound is 5-[(1E,3R)-4,4-difluoro-3-hydroxy-4-phenyl-1-buten-1-yl]-1-[6-(2H-tetrazol-5R-yl)hexyl]-2-pyrrolidinone (L-902,688). In some embodiments, the patient is recipient of a graft, wherein the graft includes at least one type of cell selected from the group consisting of hematopoietic stem cells and progenitor cells that have treated with an agonist that preferentially binds to the $EP_4$ receptor.

Some embodiments include methods of treating a donor, donor cells or a recipient of hematopoietic stem or progenitor cells, comprising the steps of: providing at least one compound that preferentially interacts with the $PGE_2$ $EP_4$ receptor, on hematopoietic stem or progenitor cells, or a pharmaceutically acceptable salt thereof; and administering a therapeutically acceptable dose of said compound to a patient in which the patient is a donor or a recipient of hematopoietic stem or progenitor cells. In many of these methods the compound increases the homing and/or the engraftment of the hematopoietic stem or progenitor cells.

Compounds that interact with the $PGE_2$ $EP_4$ receptor include, but are not limited to, compounds selected from the groups consisting of: 2-[3-[(1R,2S,3R)-3-hydroxy-2-[(E,3S)-3-hydroxy-5-[2-(methoxymethyl)phenyl]pent-1-enyl]-5-oxocyclopentyl]sulfanylpropylsulfanyl]acetic acid; methyl 4-[2-[(1R,2R,3R)-3-hydroxy-2-[(E,3S)-3-hydroxy-4-[3-(methoxymethyl)phenyl]but-1-enyl]-5-oxocyclopentyl]ethylsulfanyl]butanoate; 16-(3-Methoxymethyl)phenyl-ω-tetranor-5-thiaPGE; 5-{3-[(2S)-2-{(3R)-3-hydroxy-4-[3-(trifluoromethyl)phenyl]butyl}-5-oxopyrrolidin-1-yl]propyl]thiophene-2-carboxylate; [4'-[3-butyl-5-oxo-1-(2-trifluoromethyl-phenyl)-1,5-dihydro-[1,2,4]triazol-4-ylmethyl]-biphenyl-2-sulfonic acid (3-methyl-thiophene-2-carbonyl)-amide]; and ((Z)-7-{(1R,4S,5R)-5-[(E)-5-(3- chloro-benzo[b]thiophene-2-yl)-3-hydroxy-pent-1-enyl]-4-hydroxy-3,3-dimethyl-2-oxo-cyclopentyl}-hept-5-enoic acid) or a pharmaceutically acceptable salt thereof. Still another compound that interacts with $PGE_2$ $EP_4$ receptor and can be used in some embodiments of the invention is the compound 5-[(1E,3R)-4,4-difluoro-3-hydroxy-4-phenyl-1-buten-1-yl]-1-[6-(2H-tetrazol-5R-yl)hexyl]-2-pyrrolidinone or a pharmaceutically acceptable salt thereof.

In some embodiments recipient graft includes at least one type of cell selected from the group consisting of hematopoietic stem cells and progenitor cells that are treated with an $EP_4$ agonist. Either human or animal patients may be treated with these compounds or with cells that were first treated with these compounds either in vivo or in vitro.

Still other embodiments of the invention include methods of treating a human or an animal patient, comprising the steps of: providing a therapeutically effective amount of a $PGE_2$ $EP_4$ agonist or a pharmaceutically acceptable salt thereof; harvesting a hematopoietic stem or progenitor cell from a donor; and contacting said $PGE_2$ $EP_4$ agonist to a hematopoietic stem or progenitor cell, wherein said hematopoietic stem or progenitor cell was harvested from the donor.

Compounds that can be contacted with hematopoietic stem or progenitor cells in order to practice the invention include, but are not limited to, compounds selected from the group consisting of: 2-[3-[(1R,2S,3R)-3-hydroxy-2-[(E,3S)-3-hydroxy-5-[2-(methoxymethyl)phenyl]pent-1-enyl]-5-oxocyclopentyl]sulfanylpropylsulfanyl]acetic acid; methyl 4-[2-[(1R,2R,3R)-3-hydroxy-2-[(E,3S)-3-hydroxy-4-[3-(methoxymethyl)phenyl]but-1-enyl]-5-oxocyclopentyl]ethylsulfanyl]butanoate; 16-(3-Methoxymethyl)phenyl-ω-tetranor-5-thiaPGE; 5-{3-[(2S)-2-{(3R)-3-hydroxy-4-[3-(trifluoromethyl)phenyl]butyl}-5-oxopyrrolidin-1-yl]propyl]thiophene-2-carboxylate; [4'-[3-butyl-5-oxo-1-(2-trifluoromethyl-phenyl)-1,5-dihydro-[1,2,4]triazol-4-ylmethyl]-biphenyl-2-sulfonic acid (3-methyl-thiophene-2-carbonyl)-amide]; and ((Z)-7-{(1R,4S,5R)-5-[(E)-5-(3-chloro-benzo[b]thiophene-2-yl)-3-hydroxy-pent-1-enyl]-4-hydroxy-3,3-dimethyl-2-oxo-cyclopentyl}-hept-5-enoic acid) or a pharmaceutically acceptable salt thereof. Still another compound that can be used to practice the invention is 5-[(1E,3R)-4,4-difluoro-3-hydroxy-4-phenyl-1-buten-1-yl]-1-[6-(2H-tetrazol-5R-yl)hexyl]-2-pyrrolidinone or a pharmaceutically acceptable salt thereof. In some embodiments, hematopoietic stem or progenitor cells treated with these compounds or other $PGE_2$ $EP_4$ agonist are then administered to a human or an animal patient.

In some embodiments the therapeutically effective amount of the $PGE_2$ $EP_4$ agonist contacted with the hematopoietic stem or progenitor cells is on the order of between about 0.001 μM to about 10 μM per about $1.0 \times 10^6$ cell per ml to about $1.0 \times 10^7$ cells per ml of said hematopoietic stem or progenitor cells. In some embodiments the hematopoietic stem or progenitor cells treated and used to treat a human or animal recipient are harvested from marrow, umbilical cord or peripheral blood obtained from a human or an animal donor. In some embodiments the donor and the recipient of the hematopoietic stem or progenitor cells are the same human or animal patient.

Some embodiments of the invention include a method for altering the activity of a cell, comprising the steps of: providing a hematopoietic stem or progenitor cell, wherein the cells express at least one $PGE_2$ $EP_4$ receptor; supplying at least one compound that preferentially interacts with the $PGE_2$ $EP_4$ receptor or a pharmaceutically acceptable salt thereof; and contacting the hematopoietic stem or progenitor cell with said compound. In some embodiments the hematopoietic stem or progenitor cell are isolated from marrow, umbilical cord or peripheral blood. In some embodiments contacting the cells with the compound(s) increases the homing of said cells and or the engrafting potential of the cells. In some embodiments the compounds contacted with the cells includes, but is not limited to, at least one compound selected from the group consisting of: 2-[3-[(1R,2S,3R)-3-hydroxy-2-[(E,3S)-3-hydroxy-5-[2-(methoxymethyl)phenyl]pent-1-enyl]-5-oxocyclopentyl]sulfanylpropylsulfanyl]acetic acid; methyl 4-[2-[(1R,2R,3R)-3-hydroxy-2-[(E,3S)-3-hydroxy-4-[3-(methoxymethyl)phenyl]but-1-enyl]-5-oxocyclopentyl]ethylsulfanyl]butanoate; 16-(3-Methoxymethyl)phenyl-ω-tetranor-5-thiaPGE; 5-{3-[(2S)-2-{(3R)-3-hydroxy-4-[3-(trifluoromethyl)phenyl]butyl}-5-oxopyrrolidin-1-yl]propyl]thiophene-2-carboxylate; [4'-[3-butyl-5-oxo-1-(2-trifluoromethyl-phenyl)-1,5-dihydro-[1,2,4]triazol-4-ylmethyl]-biphenyl-2-sulfonic acid (3-methyl-thiophene-2-carbonyl)-amide]; and ((Z)-7-{(1R,4S,5R)-5-[(E)-5-(3-chloro-benzo[b]thiophene-2-yl)-3-hydroxy-pent-1-enyl]-4-hydroxy-3,3-dimethyl-2-oxo-cyclopentyl}-hept-5-enoic acid) or a pharmaceutically acceptable salt thereof. In some embodiments at least one of the compound is 5-[(1E,3R)-4,4-difluoro-3-hydroxy-4-phenyl-1-buten-1-yl]-1-[6-(2H-tetrazol-5R-yl)hexyl]-2-pyrrolidinone or a pharmaceutically acceptable salt thereof. In some embodiments the amount of therapeutically effective compound contacting said cells is about 0.001-10 microMolar. In some embodiments the number of cells treated with the compound is on the order of between about $10^6$ to about $10^7$ cells per mL.

Other aspects of the present invention provide methods of treating a donor, donor cells or a recipient of hematopoietic stem or progenitor cells comprising the step of administering to the donor, donor cells or recipient a therapeutically effective amount of an $EP_4$ agonist.

DESCRIPTION

Figure 1:
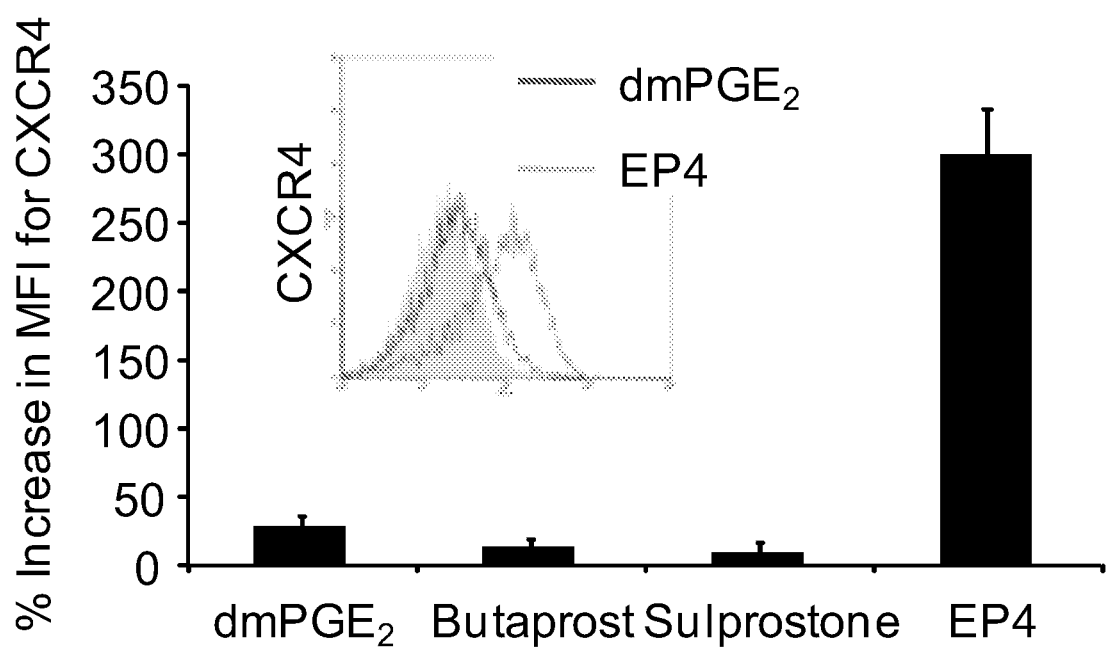
FIG. 1. Graph illustrating that treatment of cells with $EP_4$ agonist ex vivo specifically up regulates CXCR4 expression on $CD34^+$ cells.

For the purposes of promoting an understanding of the principles of the novel technology, reference will now be made to the preferred embodiments thereof, and specific language will be used to describe the same. It will nevertheless be understood that no limitation of the scope of the novel technology is thereby intended, such alterations, modifications, and further applications of the principles of the novel technology being contemplated as would normally occur to one skilled in the art to which the novel technology relates.

Unless stated otherwise the term, "therapeutically effective amount" refers to an amount of a pharmaceutically active compound that when administered to a human being or an animal patient or to a cell or collection of cells either alone or in combination with other pharmaceutically active ingredients or other components of medicaments that have a desirable effect on the physiological condition of a patient or the cell or collection of cells.

Therapeutically effective, beneficial or efficacious doses of various compounds that preferentially bind to $PGE_2$ $EP_4$ receptors administered in vivo to either a human or an animal patient are in the range of between about 0.1 mg of the compound per Kg of body weight of the patient per day to about 100 mg of the compound per Kg of body weight of the patient per day.

Compounds that preferentially bind to $PGE_2$ $EP_4$ receptors are compounds that have a higher affinity for the $EP_4$ receptor than for any of the other three EP receptors namely $EP_1$, $EP_2$ and $EP_3$.

Compounds that can be used to practice some embodiments of the invention include, but are not limited to, the following: 5-[(1E,3R)-4,4-difluoro-3-hydroxy-4-phenyl-1-buten-1-yl]-1-[6-(2H-tetrazol-5R-yl)hexyl]-2-pyrrolidinone also referred to as L-902,688 (Young, et al., 2004); 2-[3-[(1R,2S,3R)-3-hydroxy-2-[(E,3S)-3-hydroxy-5-[2-(methoxymethyl)phenyl]pent-1-enyl]-5-oxocyclopentyl] sulfanylpropylsulfanyl]acetic acid also referred to as ONO-AE1-329 (Suzawa et al., 2000); methyl 4-[2-[(1R,2R,3R)-3-hydroxy-2-[(E,3S)-3-hydroxy-4-[3-(methoxymethyl) phenyl]but-1-enyl]-5-oxocyclopentyl]ethylsulfanyl] butanoate also referred to as ONO-4819 (Maruyama et al., 2002; Ohta et al., 2009); 16-(3-Methoxymethyl)phenyl-ω-tetranor-5-thiaPGE$_1$ (Maruyama et al., 2002); 5-{3-[(2S)-2-{(3R)-3-hydroxy-4[3-(trifluoromethyl)phenyl]butyl}-5-oxopyrrolidin-1-yl]propyl]thiophene-2-carboxylate also referred to as PF-04475270 (Luu et al., 2009); APS-999 Na (El-Nefiawy et al., 2005); [4'-[3-butyl-5-oxo-1-(2-trifluoromethyl-phenyl)-1,5-dihydro-[1,2,4]triazol-4-ylmethyl]-biphenyl-2-sulfonic acid (3-methyl-thiophene-2-carbonyl)-amide](Machwate et al., 2001); and ((Z)-7-{(1R,4S,5R)-5-[(E)-5-(3-chloro-benzo[b]thiophene-2-yl)-3-hydroxy-pent-1-enyl]-4-hydroxy-3,3-dimethyl-2-oxo-cyclopentyl}-hept-5-enoic acid) U. S. Patent application number US2005/0164992A1, Jul. 28, 2005, to Donde Y, Nguyen J H, Kedzie K M, Gil D M, Donello J E and Im W B.

Unless stated otherwise the term "about" as used herein refers to range of value of plus or minus 10%, e.g., 'about 1.0' includes values between 0.9 and 1.1.

Treatment of bone marrow cells, umbilical cord blood cells, mobilized peripheral blood cells or any hematopoietic cell graft to be used for hematopoietic transplantation with Prostaglandin $E_2$ ($PGE_2$) or any active analogue or metabolite of $PGE_2$ or any E series prostaglandin with specificity for the $PGE_2$ $EP_4$ receptor, improves the homing, survival and proliferation of the transplanted hematopoietic stem cells. This treatment can be used to increase stem cell engraftment rates and thereby improve the efficiency of hematopoietic stem cell transplantation.

By some estimates the success of peripheral blood stem cell transplantation requires administration of approximately 2 million $CD34^+$ cells per kilogram of recipient patient body weight. Any agent, combination of agents or manipulations that increases the number of stem cells that can be collected, enhances their survival rates, enhances their ability to home to the appropriate marrow environment and/or enhances their self-renewal and proliferation rates will likely have a positive impact on the efficacy of hematopoietic transplantation procedures. The success of these procedures may be measured in terms of reduced patient morbidity and mortality. Numerous studies have been undertaken to try and expand the number of human hematopoietic stem cells within isolated grafts in ex vivo settings, with limited success (Broxmeyer, 2006; Haylock and Nilsson, 2007). Recently, the CXCR4 antagonist AMD3100 has been shown to enhance mobilization of stem cells (Broxmeyer, et al., 2005; Liles, et al., 2003) and in clinical trials, (Plerixafor; Mozibil) has been shown to enhance collection of mobilized stem cells when used in combination with G-CSF (DiPersio et al., 2007b; DiPersio et al., 2007a). Truncation of chemokines has been used as a method to enhance the body's ability to mobilize stem cells. Some of these methods have been patented, e.g., U.S. Pat. Nos. 6,080,398; 6,447,766B1; 639053B1; 6,713,052, each of which is incorporated by reference in its entirety. Their ability to more efficiently mobilize stem cells has also been reported (King, et al., 2001; Pelus, et al., 2004). A role for blocking the activity of a surface peptidase (CD26) has been reported as a method for enhancing the homing of hematopoietic stem cells (Christopherson, et al., 2004).

A number of agents when used in combination with G-CSF have been reported to increase the number of hematopoietic progenitor cells that can be recovered (Pelus and Fukuda, 2007; Herbert, et al., 2007), however, the ability of these agents to mobilize the long-term repopulating stem cells, i.e., the stem cells with self-renewal activity, has not been uniformly demonstrated. A recent study has shown that pulse exposure of mouse bone marrow cells to 16,16 dimethyl $pGE_2$ ($dmpGE_2$) enhances engraftment of hematopoietic stem cells, however this study provides no evidence of mechanism of action and specifically states that the effect of $PGE_2$ is not on cell homing (North, et al., 2007). It was unexpectedly demonstrated by Hoggatt, et al., 2009, that $PGE_2$ increases the CXCR4 receptor on hematopoietic stem and progenitor cells, and that this increase is responsible for increasing the homing to the bone marrow niche, resulting in a subsequent increase in engraftment.

It is generally believed that $PGE_2$ interacts with 4 highly conserved G-protein coupled receptors (GPCR); $EP_1$, $EP_2$, $EP_3$, and $EP_4$ that account for the multiple, sometimes opposing effects attributed to $PGE_2$ (Breyer, et al., 2001). EP receptor expression levels vary among different tissues, with $EP_3$ and $EP_4$ mRNA being most abundant (Sugimoto and Narumiya, 2007a) and $EP_2$ mRNA expressed at lower levels than $EP_4$ in most tissues (Katsuyama, et al., 1995). $EP_1$ activates phospholipase C (PLC) via an unidentified G protein (Tsuboi, et al., 2002), which increases intracellular $Ca^{2+}$ coupled to inositol phosphates resulting in activation of phosphokinase C (PKC) (Breyer, et al., 2001). $EP_3$ receptor ligation results in inhibition of adenylate cyclase and decreased cAMP that is $G\alpha_i$ linked (Sugimoto, et al., 2007). Multiple $EP_3$ splice variants have been identified and depending on C-terminal splicing, they can couple to multiple G proteins (Namba, et al., 1993). $EP_2$ and $EP_4$ both couple to $G_\alpha s$ leading to adenylate cyclase activation and increased cAMP, activating protein kinase A (PKA), as well as Rap1, Rac 1, and PKCζ (PKC zeta), a unique isoform implicated in HSC function (Goichberg, et al., 2006). $EP_2$ and $EP_4$ are thought to have partially redundant roles in some systems, while in others they play distinct roles (Sugimoto and Narumiya, 2007). $EP_4$ but not $EP_2$ can activate the PI3K/Akt pathway in addition to adenylate cyclase (Fujino, et al., 2003). $EP_4$ has a longer cytosolic domain allowing for more ligand dependent phosphorylation and more rapid desensitization (Nishigaki, et al., 1996) enabling a selective negative feedback loop (Sugimoto and Narumiya, 2007). Lastly, $EP_4$ is internalized when activated, while $EP_2$ is not (Desai, et al., 2000). As a consequence, $EP_2$ and $EP_4$ can have different roles based upon continuation or attenuation of signals generated by receptor activation (Breyer, et al., 2001). Treating with $PGE_2$ often exhibits a "bell-shaped" dose-response curve suggesting a different repertoire of EP receptors is activated dependent upon $PGE_2$ concentration (Hull, et al., 2004).

Most current strategies to improve hematopoietic transplantation utilizing prostaglandin have used either native $PGE_2$ or a long acting derivative of $PGE_2$, 16,16 dimethyl-prostaglandin $E_2$ ($dmPGE_2$). These prostaglandin compounds are thought to activate all 4 EP receptors leading to the numerous downstream signaling events briefly described above. As demonstrated herein, the enhancement in homing and engraftment of hematopoietic stem and progenitor cells is due to up regulation of the CXCR4 receptor by treatment with prostaglandin. Specifically focusing on the EP receptor that is responsible for the increase in CXCR4, (the $EP_4$ receptor) has the benefit of enhancing the grafting process without activating receptors that may be detrimental to the engraftment process and/or have other unknown possible deleterious consequences.

Treating With An E4 Selective Agonist Affects Homing and Engraftment Efficiency

Un-manipulated hematopoietic grafts or purified hematopoietic stem cell populations (e.g., SKL cells in mice or $CD34^+$ cells in humans) are incubated with an $EP_4$ specific agonist: 5-[(1E,3R)-4,4-difluoro-3-hydroxy-4-phenyl-1-buten-1-yl]-1-[6-(2H-tetrazol-5R-yl)hexyl]-2-pyrrolidinone (i.e. L-902,688), on ice or at room temperature at concentrations of 0.001-10 microMolar agonist per 1-10 million cells in 1 ml of culture medium, e.g. IMDM, for 15 minutes-6 hrs. After incubation, the cells are washed 3 times in sterile media or saline and administered to recipients, intravenously. L-902,688 was a generous gift from Merck Frosst (Kirkland, Canada) (Young, et al., 2004).

Referring now to FIG. 1. This graph illustrates that treatment of cells with $EP_4$ agonist ex vivo specifically up regulates CXCR4 expression on $CD34^+$ cells. The insert shows cytometry histograms of $CD34^+$ cells from cord blood samples showing significant up regulation of CXCR4 on the surface of $CD34^+$ cells after pulse exposure to $EP_4$ agonist (light line) and $dmPGE_2$ (dark line) compared to isotype control (grey shaded area). The bar graph indicator data measured from such experiments graphed as a function of different compounds used $dmPGE_2$, Butaprostone, sulprostone and $EP_4$.

Figure 2:
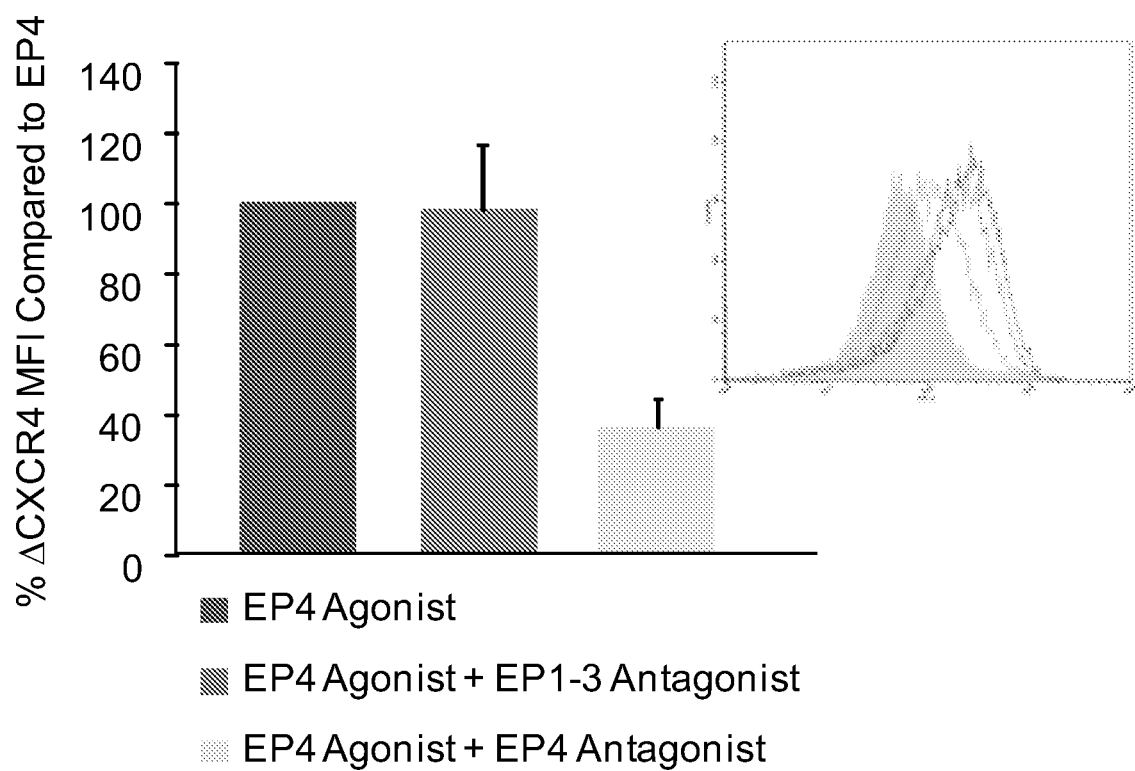
FIG. 2. Graph illustrating that signaling via the $EP_4$ receptor is responsible for up regulation of CXCR4 expression.

Referring now to FIG. 2. This graph illustrates that signaling via the $EP_4$ receptor is responsible for up regulation of CXCR4 expression. The insert shows data for 3 cord blood samples. Treatment with $EP_4$ agonist ex vivo up regulates CXCR4 expression on $CD34^+$ cells. The bar chart shows combined data for 8 samples. The bar chart data demonstrates that ex vivo treatment with $EP_4$ agonist up regulates CXCR4 by about 3 fold. In the bar chart this effort is normalized to 100%. Pretreatment of cells with a specific antagonist of the EP 1, 2 and 3 receptor prior to exposure to $EP_4$ antagonist had no effect on up regulation of CXCR4 whereas pre-incubation with a selective $EP_4$ antagonist prior to exposure to $EP_4$ agonist significantly blocked up regulation of CXCR4. The fact that up regulation of CXCR4 by an $EP_4$ selective agonist is blocked by a selective $EP_4$ antagonist, but not by EP1, 2, 3, antagonist, provides additional evidence that up regulation is mediated through the $EP_4$ receptor.

Additional embodiments include administering $EP_4$ agonists (e.g., on the order of about 0.001-10 microMolar) to patients immediately prior to and daily afterwards after receiving a hematopoietic graft as a means of enhancing stem cell function. Therapeutic effective doses are amounts of the pharmaceutically active agent used either alone or in combination with another pharmaceutical agent or inert material that has a beneficial effect on a so treated human or animal patient. Such benefits may include, but are not limited to, increasing the effectiveness of other steps in a given treatment regimen.

While the novel technology has been illustrated and described in detail in the figures and foregoing description, the same is to be considered as illustrative and not restrictive in character, it being understood that only the preferred embodiments have been shown and described and that all changes and modifications that come within the spirit of the novel technology are desired to be protected. As well, while the novel technology was illustrated using specific examples, theoretical arguments, accounts, and illustrations, these illustrations and the accompanying discussion should by no means be interpreted as limiting the technology. All patents, patent applications, and references to texts, scientific treatises, publications, and the like referenced in this application are incorporated herein by reference in their entirety.

REFERENCES

Breyer, R. M., Bagdassarian, C. K., Myers, S. A., and Breyer, M. D. (2001). Prostanoid receptors: subtypes and signaling. Annu Rev. Pharmacol. Toxicol. 41, 661-690.

Broxmeyer, H. E. (2006). Cord Blood Hematopoietic Stem and Progenitor Cells. In Essentials of Stem Cell Biology, Elsevier, Inc.), pp. 133-137.

Broxmeyer, H. E., Orschell, C. M., Clapp, D. W., Hangoc, G., Cooper, S., Plett, P. A., Liles, W. C., Li, X., Graham-Evans, B., Campbell, T. B., Calandra, G., Bridger, G., Dale, D. C., and Srour, E. F. (2005). Rapid mobilization of murine and human hematopoietic stem and progenitor cells with AMD3100, a CXCR4 antagonist. J. Exp. Med. 201, 1307-1318.

Christopherson, K. W., Hangoc, G., Mantel, C. R., and Broxmeyer, H. E. (2004). Modulation of hematopoietic stem cell homing and engraftment by CD26. Science 305, 1000-1003.

Desai, S., April, H., Nwaneshiudu, C., and Ashby, B. (2000). Comparison of agonist-induced internalization of the human EP2 and EP4 prostaglandin receptors: role of the carboxyl terminus in EP4 receptor sequestration. Mol. Pharmacol. 58, 1279-1286.

DiPersio, J. F., Micallef, I., Stiff, P., Bolwell, B. J., Maziarz, R. T., Angell, J., Bridger, G., and Calandra, G. A phase III, multicenter, randomized, double bnlind, placebo-controlled, comparative trial of AMD3100 (Perixafor)+G-CSF vs. G-CSF+placebo for mobilization in Non-Hodgkins Lymphoma (NHL) patients for autologous hematopoietic stem cell (aHSC) transplantation. Blood 110, 185a. 2007a.
Ref Type: Abstract DiPersio, J. F., Stadtmauer, A. P., Nademanee, A. P., Stiff, P., Micallef, I., Angell, J., Bridger, G., and Calandra, G. A phase III, multicenter, randomized, double bnlind, placebo-controlled, comparative trial of AMD3100 (Perixafor)+G-CSF vs. G-CSF+placebo for mobilization in multiple myeloma (MM) patients for autologous hematopoietic stem cell (aHSC) transplantation. Blood 110, 137a. 2007b.
Ref Type: Abstract El-Nefiawy, N., Abdel-Hakim, K., and Kanayama, N. (2005). The selective prostaglandin EP4 agonist, APS-999 Na, induces follicular growth and maturation in the rat ovary. Eur. J. Endocrinol. 152, 315-323.

Fujino H, Xu W, Regan J W. Prostaglandin E2 induced functional expression of early growth response factor-1 by EP4, but not EP2, prostanoid receptors via the phosphatidylinositol 3-kinase and extracellular signal-regulated kinases. J. Biol. Chem. 2003; 278:12151-12156.

Goichberg P, Kalinkovich A, Borodovsky N et al. cAMP-induced PKCzeta activation increases functional CXCR4 expression on human CD34+hematopoietic progenitors. Blood 2006; 107:870-879.

Haylock, D. N. and Nilsson, S. K. (2007). Expansion of umbilical cord blood for clinical transplantation. Curr Stem Cell Res Ther 2, 324-335.

Herbert, K. E., Walkley, C. R., Winkler, I. G., Hendy, J., Olsen, G. H., Yuan, Y. D., Chandraratna, R. A., Prince, H. M., Levesque, J. P., and Purton, L. E. (2007). Granulocyte colony-stimulating factor and an RARalpha specific agonist, VTP195183, synergize to enhance the mobilization of hematopoietic progenitor cells. Transplantation 83, 375-384.

Hull, M. A., Ko, S. C., and Hawcroft, G. (2004). Prostaglandin EP receptors: targets for treatment and prevention of colorectal cancer? Mol. Cancer Ther. 3, 1031-1039.

Katsuyama, M., Nishigaki, N., Sugimoto, Y., Morimoto, K., Negishi, M., Narumiya, S., and Ichikawa, A. (1995). The mouse prostaglandin E receptor EP2 subtype: cloning, expression, and northern blot analysis. FEBS Lett. 372, 151-156.

King, A. G., Horowitz, D., Dillon, S. B., Levin, R., Farese, A. M., MacVittie, T. J., and Pelus, L. M. (2001). Rapid mobilization of murine hematopoietic stem cells with enhanced engraftment properties and evaluation of hematopoietic progenitor cell mobilization in rhesus monkeys by a single injection of SB-251353, a specific truncated form of the human CXC chemokine GRObeta. Blood 97, 1534-1542.

Liles, W. C., Broxmeyer, H. E., Rodger, E., Wood, B., Hubel, K., Cooper, S., Hangoc, G., Bridger, G. J., Henson, G. W., Calandra, G., and Dale, D. C. (2003). Mobilization of hematopoietic progenitor cells in healthy volunteers by AMD3100, a CXCR4 antagonist. Blood 102, 2728-2730.

Luu, K. T., Zhang, E. Y., Prasanna, G., Xiang, C., Anderson, S., Fortner, J., and Vicini, P. (2009). Pharmacokinetic-pharmacodynamic and response sensitization modeling of the intraocular pressure-lowering effect of the EP4 Agonist 5-{3-[(2S)-2-{(3R)-3-hydroxy-4-[3-(trifluoromethyl)phenyl]butyl}-5-oxopyrr olidin-l-yl]propyl}thiophene-2-carboxylate (PF-04475270). J. Pharmacol. Exp Ther. 331, 627-635.

Machwate, M., Harada, S., Leu, C. T., Seedor, G., Labelle, M., Gallant, M., Hutchins, S., Lachance, N., Sawyer, N., Slipetz, D., Metters, K. M., Rodan, S. B., Young, R., and Rodan, G. A. (2001). Prostaglandin receptor EP(4) mediates the bone anabolic effects of PGE(2). Mol. Pharmacol. 60, 36-41.

Maruyama, T., Kuwabe, S. I., Kawanaka, Y., Shiraishi, T., Shinagawa, Y., Sakata, K., Seki, A., Kishida, Y., Yoshida, H., Maruyama, T., Ohuchida, S., Nakai, H., Hashimoto, S., Kawamura, M., Kondo, K., and Toda, M. (2002). Design and synthesis of a selective EP4-receptor agonist. Part 4: practical synthesis and biological evaluation of a novel highly selective EP4-receptor agonist. Bioorg. Med. Chem. 10, 2103-2110.

Namba T, Sugimoto Y, Negishi M et al. Alternative splicing of C-terminal tail of prostaglandin E receptor subtype EP3 determines G-protein specificity. Nature 1993; 365:166-170.

Nishigaki, N., Negishi, M., and Ichikawa, A. (1996). Two Gs-coupled prostaglandin E receptor subtypes, EP2 and EP4, differ in desensitization and sensitivity to the metabolic inactivation of the agonist. Mol. Pharmacol. 50, 1031-1037.

North, T. E., Goessling, W., Walkley, C. R., Lengerke, C., Kopani, K. R., Lord, A. M., Weber, G. J., Bowman, T. V., Jang, I. H., Grosser, T., Fitzgerald, G. A., Daley, G. Q., Orkin, S. H., and Zon, L. I. (2007). Prostaglandin E2 regulates vertebrate haematopoietic stem cell homeostasis. Nature 447, 1007-1011.

Ohta, C., Kuwabe, S. I., Shiraishi, T., Shinohara, I., Araki, H., Sakuyama, S., Makihara, T., Kawanaka, Y., Ohuchida, S., and Seko, T. (2009). An improved synthesis of the selective EP4 receptor agonist ONO-4819. J. Org. Chem. 74, 8298-8308.

Pelus, L. M., Bian, H., King, A. G., and Fukuda, S. (2004). Neutrophil-derived MMP-9 mediates synergistic mobilization of hematopoietic stem and progenitor cells by the combination of GCSF and the chemokines GRObeta/CXCL2 and GRObetaT/CXCL2delta4. Blood 103, 110-119.

Pelus, L. M. and Fukuda, S. (2007). Chemokine-mobilized adult stem cells; defining a better hematopoietic graft. Leukemia.

Sugimoto, Y. and Narumiya, S. (2007a). Prostaglandin E receptors. J. Biol. Chem. 282, 11613-11617.

Suzawa, T., Miyaura, C., Inada, M., Maruyama, T., Sugimoto, Y., Ushikubi, F., Ichikawa, A., Narumiya, S., and Suda, T. (2000). The role of prostaglandin E receptor subtypes (EP1, EP2, EP3, and EP4) in bone resorption: an analysis using specific agonists for the respective EPs. Endocrinology 141, 1554-1559.

Tsuboi, K., Sugimoto, Y., and Ichikawa, A. (2002). Prostanoid receptor subtypes. Prostaglandins Other Lipid Mediat. 68-69, 535-556.

Young, R. N., Billot, X., Han, Y., Slipetz, D. A., Chauret, N, Belley, M., Metters, K., Mathieu, M, C., Greig, G. M., Denis, D., (2004), Discovery and synthesis of a potent, selective and orally bioavailable EP4 receptor agonist. Heterocycles 64: 437-466.

We claim:
1. A method of increasing homing of a hematopoietic stem cell or hematopoietic progenitor cell, comprising the steps of:
(a) contacting a hematopoietic stem cell or hematopoietic progenitor cell expressing at least one PGE2 EP4 receptor with at least one compound or a pharmaceutically acceptable salt thereof such that homing potential is increased in the contacted hematopoietic stem cell or hematopoietic progenitor cell,
wherein the at least one compound or the pharmaceutically acceptable salt thereof:
(i) preferentially interacts with the PGE2 EP4 receptor as compared to the PGE2 EP1, EP2, and EP3 receptors, and
(ii) increases the homing of the contacted hematopoietic stem cell or hematopoietic progenitor cell when transplanted into a patient compared to a compound that does not preferentially interact with the PGE2 EP4 receptor, and
(b) washing the contacted hematopoietic stem cell or hematopoietic progenitor cell, and wherein the amount of the compound contacting said hematopoietic stem cell or hematopoietic progenitor cell is about 0.001-10 microMolar.
2. The method according to claim 1, wherein said hematopoietic stem cell or hematopoietic progenitor cell is isolated from marrow, umbilical cord or peripheral blood.

3. The method according to claim 1, wherein contacting the compound with said hematopoietic stem cell or hematopoietic progenitor cell increases the homing of said cells.

4. The method according to claim 1, wherein contacting the compound with said hematopoietic stem cell or hematopoietic progenitor cell increases the engrafting potential of said cells.

5. The method according to claim 1, wherein the at least one compound is selected from the groups consisting of: 2-[3-[(1R,2S,3R)-3-hydroxy-2-[(E,3S)-3-hydroxy-5-[2-(methoxymethyl)phenyl-]pent-l-enyl]-5-oxocyclopentyl] sulfanylpropylsulfanyl]acetic acid;
methyl 4-[2-[(1R,2R,3R)-3-hydroxy-2-[(E,3S)-3-hydroxy-4-[3-(methoxymethyl)phenyl-]but-1-enyl]-5-oxocyclopentyl]ethylsulfanyl]butanoate; 16-(3-Methoxymethyl)phenyl-w-tetranor-5-thiaPGE; 543-[(2S)-2-{(3R)-3-hydroxy-4-[3-(trifluoromethyl) phenyl]butyl}-5-oxopyrrolidin-1-yl]propyl]thiophene-2-carboxylate; [4'-[3-butyl-5-oxo-1-(2-trifluoromethyl-phenyl)-1,5-dihydro-[1,2,4]triazol-4-ylmethyl]-biphenyl-2-sulfonic acid (3-methyl-thiophene-2-carbonyl)-amide]; and ((Z)-7-{(1R,4S,5R)-5-[(E)-5-(3-chloro-benzo[b]thiophene-2-yl)-3-hydroxy-p-ent-l-enyl]-4-hydroxy-3,3-dimethyl-2-oxo-cyclopentyl}-hept-5-enoic acid) or a pharmaceutically acceptable salt thereof.

6. The methods according to claim 1, wherein the at least one compound is 5-[(1E,3R)-4,4-difluoro-3-hydroxy-4-phenyl-1-buten-1-yl]-1-[6-(2H-tetrazol-5Ryl) hexyl]-2-pyrrolidinone or a pharmaceutically acceptable salt thereof.

7. The method according to claim 1, wherein said cell is contacted with said compound or pharmaceutically acceptable salt thereof for 15 minutes to 6 hours.

8. The method according to claim 1, further comprising administering the washed cell to the patient.

9. A method of increasing homing of a hematopoietic stem cell or hematopoietic progenitor cell, comprising the steps of:
(a) contacting about 1-10 million hematopoietic stem cells or hematopoietic progenitor cells expressing at least one PGE2 EP4 receptor with at least one compound or a pharmaceutically acceptable salt thereof such that homing potential is increased in the contacted hematopoietic stem cell or hematopoietic progenitor cell, wherein the compound or the pharmaceutically acceptable salt thereof:
(i) preferentially interacts with the PGE2 EP4 receptor as compared to PGE2 EP1, EP2, and EP3 receptors, and
(ii) increases the homing potential of the contacted hematopoietic stem cell or hematopoietic progenitor cells compared to a compound that does not preferentially interact with the PGE2 EP4 receptor, and
(b) washing the contacted hematopoietic stem cell or hematopoietic progenitor cell, and wherein the amount of the compound contacting said hematopoietic stem cells or hematopoietic progenitor cells is about 0.001-10 microMolar.

10. The method of claim 1, wherein the contacted hematopoietic stem cell or hematopoietic progenitor cell has increased engraftment when transplanted into a patient compared to a non-contacted hematopoietic stem cell or hematopoietic progenitor cell.

* * * * *

UNITED STATES PATENT AND TRADEMARK OFFICE
CERTIFICATE OF CORRECTION

PATENT NO. : 11,459,545 B2
APPLICATION NO. : 13/509409
DATED : October 4, 2022
INVENTOR(S) : Louis M. Pelus et al.

It is certified that error appears in the above-identified patent and that said Letters Patent is hereby corrected as shown below:

In the Claims

Column 11, Line 16, Claim 5, "w-tetranor" should be -- ω-tetranor --.

Column 11, Line 16, Claim 5, "543" should be -- 5-{3 --.

Signed and Sealed this
Twelfth Day of November, 2024

Katherine Kelly Vidal
*Director of the United States Patent and Trademark Office*